US011517332B2

(12) United States Patent
Fiechter et al.

(10) Patent No.: US 11,517,332 B2
(45) Date of Patent: Dec. 6, 2022

(54) PATIENT-SPECIFIC NAVIGATION GUIDE

(71) Applicant: MEDACTA INTERNATIONAL SA, Castel San Pietro (CH)

(72) Inventors: Meinrad Fiechter, Castel San Pietro (CH); Yuri Insinna, Castel San Pietro (CH); Francesco Siccardi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 0 days.

(21) Appl. No.: 17/281,900

(22) PCT Filed: Sep. 26, 2019

(86) PCT No.: PCT/IB2019/058162
§ 371 (c)(1),
(2) Date: Mar. 31, 2021

(87) PCT Pub. No.: WO2020/074990
PCT Pub. Date: Apr. 16, 2020

(65) Prior Publication Data
US 2021/0346038 A1 Nov. 11, 2021

(30) Foreign Application Priority Data
Oct. 8, 2018 (IT) .................. 102018000009227

(51) Int. Cl.
*A61B 17/17* (2006.01)
*A61B 17/70* (2006.01)
(Continued)

(52) U.S. Cl.
CPC ...... *A61B 17/1757* (2013.01); *A61B 17/7055* (2013.01); *A61B 17/7067* (2013.01);
(Continued)

(58) Field of Classification Search
CPC ............ A61B 17/1757; A61B 17/7055; A61B 17/7067; A61B 17/7083; A61B 2017/0023; A61B 2017/568
See application file for complete search history.

(56) References Cited

U.S. PATENT DOCUMENTS

| 5,112,337 A | 5/1992 | Palous et al. |
| 5,928,232 A | 7/1999 | Howland et al. |

(Continued)

FOREIGN PATENT DOCUMENTS

| CN | 206560458 | 10/2017 |
| DE | 4219939 | 12/1993 |

(Continued)

OTHER PUBLICATIONS

Office Action issued for U.S. Appl. No. 16/333,057, dated Jul. 30, 2020.
(Continued)

*Primary Examiner* — Eduardo C Robert
*Assistant Examiner* — Tara Rose E Carter
(74) *Attorney, Agent, or Firm* — Meunier Carlin & Curfman LLC

(57) ABSTRACT

A patient-specific navigation guide for use in spinal surgery including a first and a second guide member, both integral with a supporting frame and extending along a respective longitudinal development axis from a proximal opening to a distal opening for guiding surgical instruments on a first vertebra of a patient. The guide also includes contact members designed to match with a corresponding plurality of contact areas on a first and on a second vertebra of the patient to define a single coupling configuration of the patient-specific navigation guide on the patient's vertebrae. The first and second guide members are substantially opposite with respect to a median plane orthogonal to a straight
(Continued)

line joining the longitudinal axes of the first and second guide members. The navigation guide also comprises a single additional third guide member that is integral with the frame and is adapted to abut on a second vertebra.

8 Claims, 6 Drawing Sheets

(51) Int. Cl.
*A61B 17/00* (2006.01)
*A61B 17/56* (2006.01)

(52) U.S. Cl.
CPC .. *A61B 17/7083* (2013.01); *A61B 2017/0023* (2013.01); *A61B 2017/568* (2013.01)

(56) References Cited

U.S. PATENT DOCUMENTS

| | | |
|---|---|---|
| 8,758,357 B2 | 6/2014 | Frey |
| 8,870,889 B2 | 10/2014 | Frey |
| 9,198,678 B2 | 12/2015 | Frey et al. |
| 9,642,633 B2 | 5/2017 | Frey et al. |
| 9,987,024 B2 | 6/2018 | Frey et al. |
| 2002/0123668 A1 | 9/2002 | Ritland |
| 2007/0066977 A1 | 3/2007 | Assell et al. |
| 2008/0114370 A1 | 5/2008 | Schoenfeld |
| 2011/0319745 A1 | 12/2011 | Frey |
| 2012/0130382 A1 | 5/2012 | Iannotti et al. |
| 2012/0245587 A1 | 9/2012 | Fang et al. |
| 2013/0053854 A1 | 2/2013 | Schoenefeld et al. |
| 2013/0123850 A1* | 5/2013 | Schoenefeld ...... A61B 17/7055 606/248 |
| 2013/0218163 A1 | 8/2013 | Frey |
| 2014/0074099 A1 | 3/2014 | Vigneron et al. |
| 2014/0358152 A1* | 12/2014 | Condino ............ A61B 17/1757 606/96 |
| 2018/0042619 A1 | 2/2018 | Frey et al. |
| 2018/0177512 A1 | 6/2018 | Hogan et al. |
| 2021/0077119 A1 | 3/2021 | Siccardi et al. |

FOREIGN PATENT DOCUMENTS

| | | |
|---|---|---|
| DE | 102016218965 | 4/2018 |
| EP | 2502582 | 9/2012 |
| EP | 2749235 A1 | 7/2014 |
| JP | 2015208566 | 11/2015 |
| JP | 2016524506 | 8/2016 |
| TW | 200908927 | 3/2009 |
| TW | 201 238 556 A | 10/2012 |
| WO | 9600049 | 1/1996 |
| WO | 2012156466 | 11/2012 |
| WO | 2013158521 | 10/2013 |
| WO | 2014070889 | 5/2014 |
| WO | 2014090908 A1 | 6/2014 |
| WO | 2014197844 | 12/2014 |
| WO | 2016075581 | 5/2016 |
| WO | 2016075660 | 5/2016 |
| WO | 2018055494 | 3/2018 |
| WO | 2018055518 | 3/2018 |

OTHER PUBLICATIONS

Office Action issued for U.S. Appl. No. 16/333,055, dated Dec. 8, 2020.
International Search Report and Written Opinion for International Application No. PCT/IB2019/058162 dated Jan. 22, 2020, 16 pages.
Berry et al., Personalised image-based templates for intra-operative guidance, Proceedings of the Institution of Mechanical Engineers, Part H: Journal of Engineering in Medicine, vol. 219, pp. 111-118, 2004.
Brussel et al., Medical Image-Based Design of An Individualized Surgical Guide For Pedicle Screw Insertion, 18th Annual International Conference of the IEEE Engineering in Medicine and Biology Society, Amsterdam, pp. 225-226, 1996.
Lu et al., A novel computer-assisted drill guide template for placement of C2 laminar screws, Eur Spine J, vol. 18, pp. 1379-1385, 2009.
Lu et al., A Novel Patient-Specific Navigational Template for Cervical Pedicle Screw Placement. SPINE, vol. 34, No. 26, pp. E959-E964, 2009.
Lu et al., Rapid prototyping drill guide template for lumbar pedicle screw placement, Chinese Journal of Traumatology, vol. 12(3), pp. 171-177, 2009.
Popescu et al., Design and Rapid Manufacturing Of Patient-Specific Spinal Surgical Guides: A Survey, Proceedings in Manufacturing Systems, vol. 7, Issue 2, pp. 115-120, 2012.
Radermacher, Klaus, Computer Assisted Orthopaedic Surgery with Individual Templates, Helmholtz-Institute for Biomedical Engineering, 2 pages, 1997.
Ryken et al., Image-based drill templates for cervical pedicle screw placement, J Neurosurg Spine vol. 10, pp. 21-26, 2009.
English Translation of Notice of Reasons of Refusal in JP 2019-536354, dated Feb. 10, 2020, 7 pages.
International Search Report and Written Opinion issued for Application No. PCT/IB2017/055688, dated Nov. 16, 2017. 11 pages.
International Search Report and Written Opinion issued for Application No. PCT/IB2017/055588, dated Nov. 22, 2017. 13 pages.
English Translation of Notice of Reasons of Refusal in JP 2019-536348, dated Feb. 27, 2020, 14 pages.
International Search Report and Written Opinion issued for Application No. PCT/IB2019/053765 dated Aug. 6, 2019, 15 pages.
International Search Report and Written Opinion, issued by the International Searching Authority (ISA/EP) in Application No. PCT/IB2018/060161 dated Apr. 5, 2019. 9 pages.
International Search Report and Written Opinion, issued by the International Searching Authority (ISA/EP) in Application No. PCT/IB2019/060161 dated Apr. 2, 2020. 11 pages.
International Search Report and Written Opinion, issued by the International Searching Authority (ISA/EP) in Application No. PCT/IB2018/060160 dated Apr. 5, 2019. 13 pages.
Office Action issued for U.S. Appl. No. 16/956,253, dated Oct. 12, 2021.
Notice of Allowance received in connection with U.S. Appl. No. 16/956,253, dated Feb. 8, 2022, 10 pages.

* cited by examiner

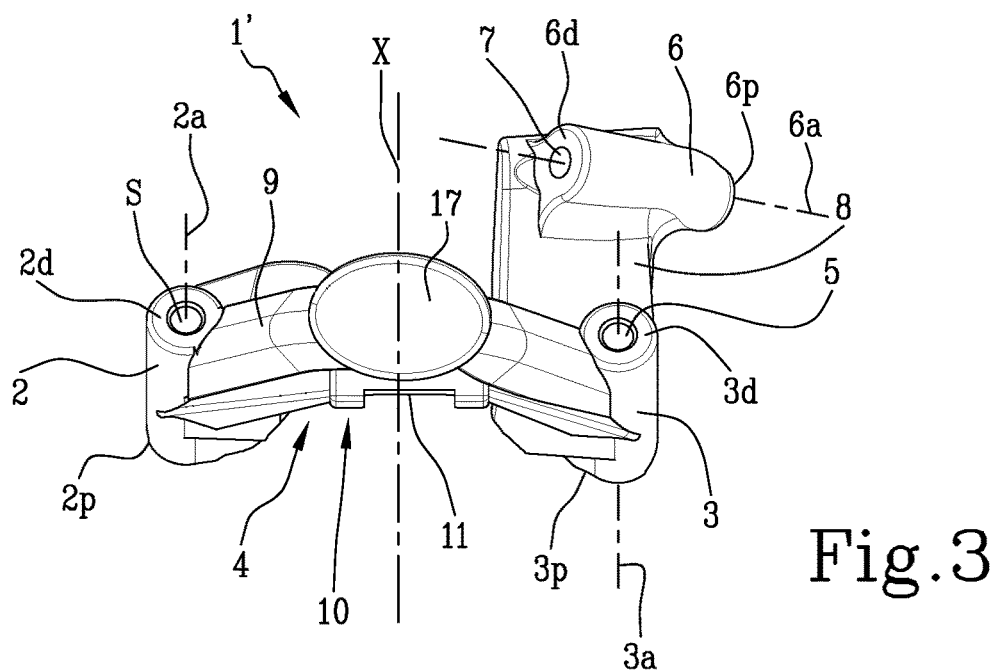
Fig.3
Fig.4
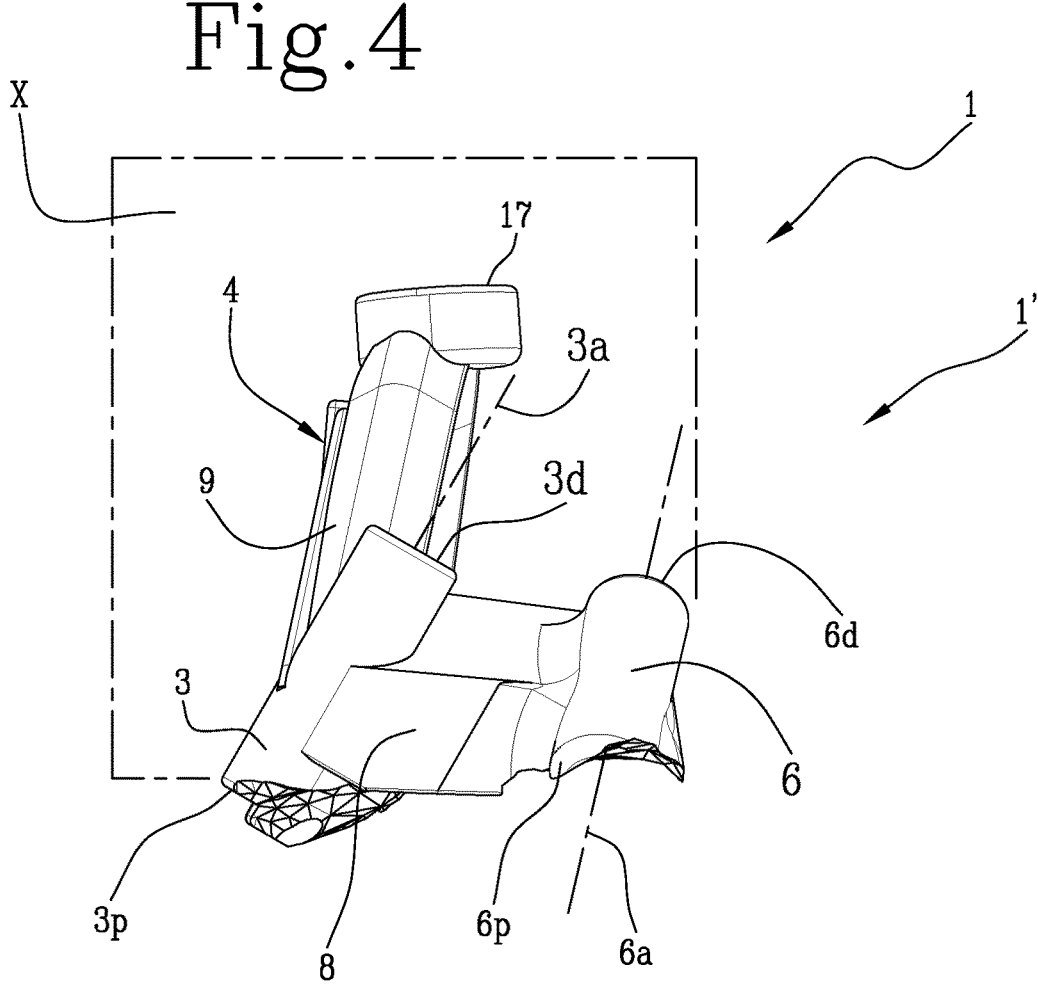

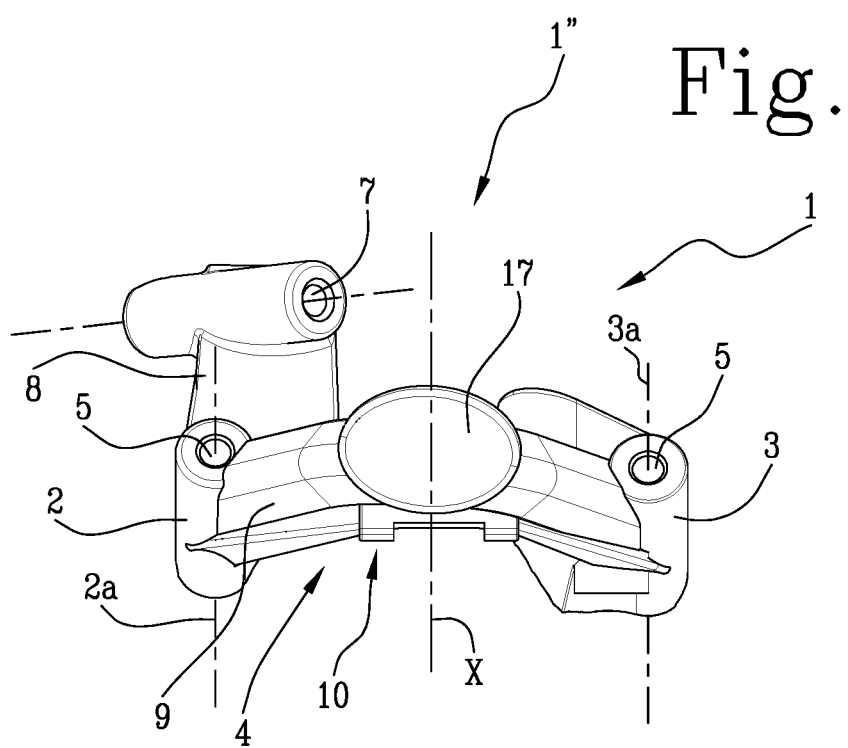
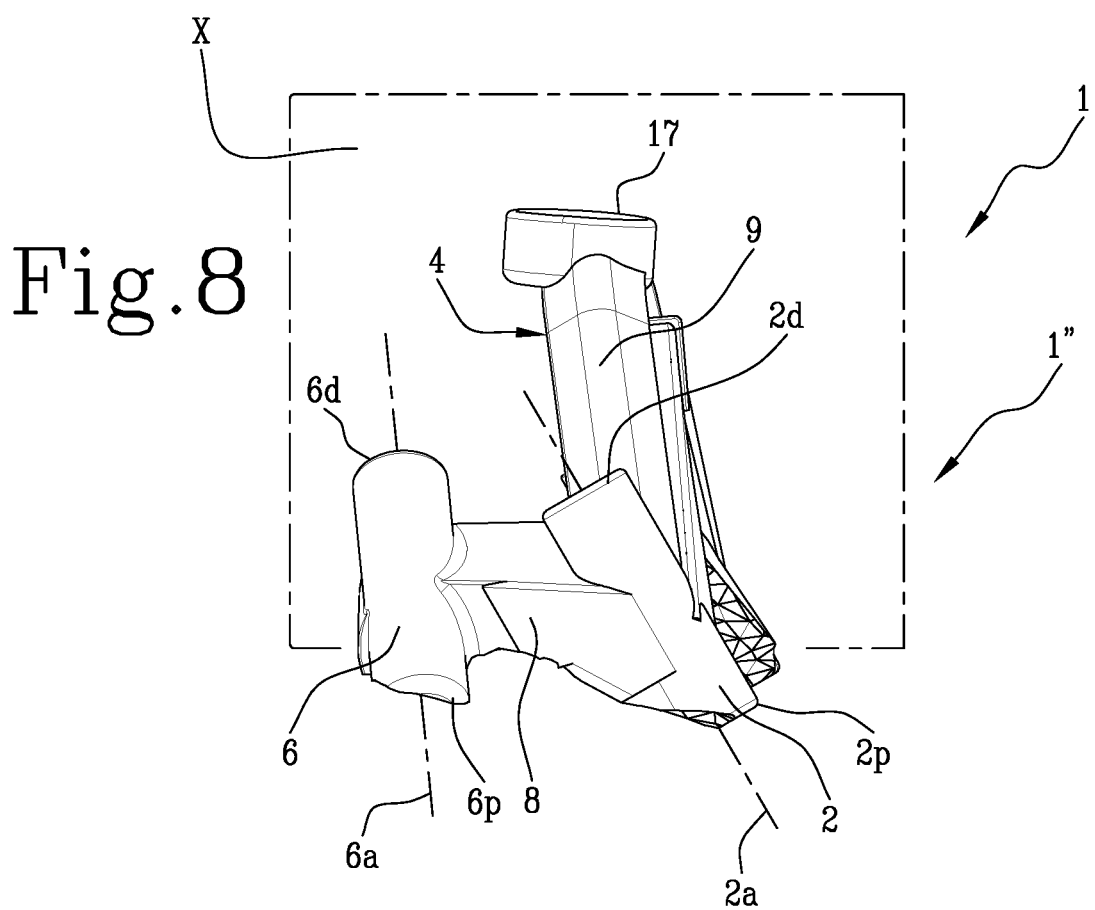

PATIENT-SPECIFIC NAVIGATION GUIDE

TECHNICAL FIELD

The present invention relates to the technical field of orthopaedic surgery. More specifically, the invention relates to a patient-specific navigation guide for the spine to be employed in spinal surgery.

PRIOR ART

Patient-specific guides are disposable templates, which are individually designed to match the anatomy of the bone derived from computer tomography images of a given patient. Surgical operations, such as perforations and cuts, can be planned in the pre-operative phase by using computer-assisted technologies, and the resulting patient-specific guides allow the surgeon to then accurately replicate the planned operations on the patient's body.

Patient-specific guides have been employed in various fields of orthopaedic surgery, including spinal surgery.

In this field, patient-specific guides are primarily employed to assist the surgeon during the insertion of the pedicle screw, so that the screw can be inserted inside the bone structure in an optimal pre-planned insertion direction.

The sacral vertebrae have a different shape with respect to the cervical, thoracic or lumbar vertebrae. In the specific case of pathologies connected to the last lumbar vertebrae, such as spondylolisthesis—a pathology that occurs when the fifth lumbar vertebra (L05) slides forward towards the abdomen with respect to the first sacral vertebra (S01)—or in the case of scoliosis or lordosis, it is necessary to operate on the first sacral vertebrae, particularly on the S01 and S02.

The guides currently used for these operations are quite large in size, with four tubular guide members having to operate simultaneously on two adjacent vertebrae, the S01 and S02.

Since spinal surgery tends to be carried out by using minimally invasive surgery, the tendency is to reduce the size of the wound to a minimum. In light of this, when operating on the first sacral vertebrae, the S01 and S02, the surgeon's objective is to reduce the size of the cut as much as possible, limiting its length as much as possible. For example, when the operation involves intervention on the L05, S01 and S02, the cut, in the prior art, must still be made from the L05 down to S02.

To insert these known navigation guides, the cut must be quite extensive to be able to enlarge the wound, insert and position the guide.

If the cut is extended, the surgery is no longer minimally invasive, with a consequent lengthening of the operating and recovery times for the patient during convalescence. Moreover, such a cut extends to particularly mobile areas of the skin, such as near the coccyx, where the wound struggles to heal.

The navigation guides known and described, for example in EP2749235, EP 3217895 or EP2502582, cannot be used in posterior sacroiliac or sacro-alar fixation surgery (S02-AI screws), as they are limited to the S01 level and optimized for a converging or slightly divergent trajectory for screws in the posterior-anterior direction (whereas the typical trajectories for S02-AI screws are strongly divergent). In addition, the mask would be too cumbersome with respect to the incision required for S02-AI screws, and would also have greater instability due to the surgical techniques used to implant the S02 screws.

The purpose of the present invention is to overcome the drawbacks of the prior art. In particular, the purpose of the present invention is to propose a patient-specific navigation guide that is not cumbersome and that can be used with the S01 and S02 vertebrae in minimally invasive surgery.

Another purpose of the present invention is to create a patient-specific navigation guide that allows the screws to be inserted safely and precisely, even with difficult trajectories, without continuous beam control.

The purpose of the present invention is also to provide a patient-specific navigation guide that can provide simplified positioning on the patient's bone structure in a stable and safe manner.

These and other purposes and advantages are achieved by a patient-specific navigation guide as described in the accompanying claims and by a specific navigation kit in accordance with claim 10.

SUMMARY

A first aspect of the present invention involves a patient-specific navigation guide for use in spinal surgery, comprising a first and a second guide member both of which are integral with a supporting frame and extending along a respective longitudinal development axis from a proximal opening to a distal opening for guiding surgical instruments on a first vertebra of a patient. The guide also involves contact members designed to match a corresponding plurality of contact areas on the patient's vertebrae in order to define a unique coupling configuration of the patient-specific navigation guide on the patient's vertebrae. The first and second guide members are substantially opposite to a median plane orthogonal to a straight line joining the longitudinal axes of the two guide members.

The first and second guide members can, preferably, be associated with the first vertebra.

The guide also comprises a single additional guide member in addition to the first two, in particular a third guide member adapted to abut, by juxtaposition, on a second vertebra adjacent to and consecutive to the first.

The navigation guide comprises, in total, three guide members: the first two are symmetrical with respect to a median plane orthogonal to a straight line joining the longitudinal axes of the two guide members, and a third guide member only connected to the first or second guide member.

The third guide member is preferably integral with the supporting frame through a plate connected to the first or second guide member.

Advantageously, the plate extends from said supporting frame in the caudal direction along the patient's spine when in use.

The three guide members are preferably tubular.

Advantageously, the third guide member extends along a respective longitudinal development axis from a proximal opening to a distal opening for guiding surgical instruments on the second vertebra adjacent to the first; the longitudinal development axis is transverse to the median plane and to the longitudinal development axes of the first and second guide members.

The plate preferably defines at a proximal surface thereof, i.e. on the side facing the patient's vertebra, a contact surface with the lamina of the patient's second vertebra.

Advantageously, the supporting frame comprises a bridge connecting the first and the second guide member. The bridge also comprises a main contact member adapted to being coupled with the spinous process or sacral crest of the first vertebra.

The bridge shall preferably comprise, substantially above the main contact member, a gripping element that also acts as a pressure element for holding the device in place during use.

Advantageously, there is a notch, below the contact member of the bridge, which is adapted to accommodate the spinous process or sacral crest.

A second aspect of the present invention involves a patient-specific navigation guide kit comprising two navigation guides in which a first guide has the third guide member connected to the first guide member through a plate to allow one side of a second vertebra to be pierced. The kit also comprises a second guide that has the third guide member connected to the second guide member through a respective plate to allow the side of the second vertebra opposite to the longitudinal line of the vertebral column, to which the first and second vertebra belong, to be pierced.

BRIEF DESCRIPTION OF THE FIGURES

A patient-specific navigation guide as described and claimed is also shown in the following illustrative and non-exhaustive figures, wherein:

FIG. 3 is a view from above of the guide shown in FIG. 1;

FIG. 4 is a lateral view of the guide shown in FIG. 1;

FIG. 7 is a view from above of the guide shown in FIG. 1;

FIG. 8 is a lateral view of the guide shown in FIG. 1

DESCRIPTION

Figure 1:
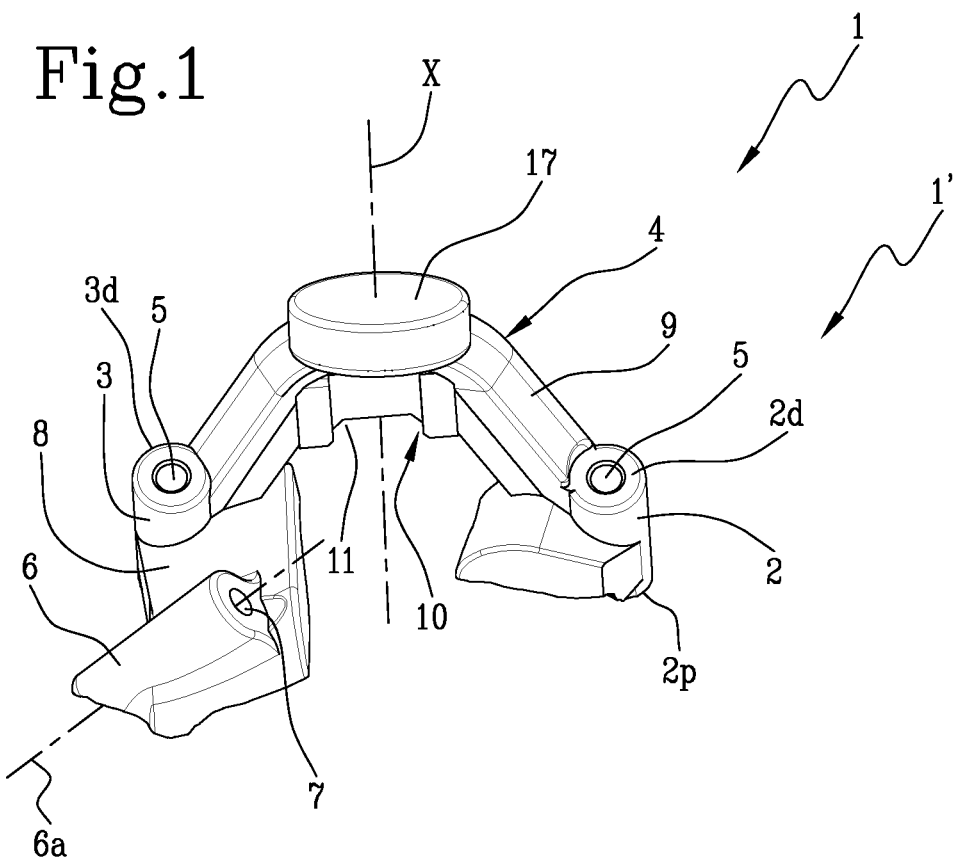
FIG. 1 is a perspective view of a first patient-specific navigation guide according to the present invention.

With reference to the attached figures, the number 1 indicates a patient-specific navigation guide in accordance with a first aspect of the present invention.

This guide 1 is structured in such a way as to operate on a first vertebra 100, in particular the S01, and on a second vertebra 200, in particular the S02, which is adjacent to and consecutive to the first vertebra 100.

The guide 1 comprises a first 2 and a second 3 guide member, preferably tubular, both of which are integral with a supporting frame 4.

Both the first 2 and the second 3 guide member extend along a respective longitudinal development axis $2a$ and $3a$, from a respective proximal opening $2p$, $3p$ to a respective distal opening $2d$, $3d$ and each has an internal channel 5 along its respective longitudinal axis $2a$, $3a$.

In the following description, the terms proximal and distal refer to the patient.

These guide members 2 and 3 accommodate, within their axial channels 5, surgical instruments, such as a Kirschner wire, a cannulated drill bit or a screw or the like, which are adapted to operating on the first vertebra 100 of a patient.

As can be seen in the attached figures, the first 2 and the second 3 guide members are substantially symmetrical to a median plane X orthogonal to a straight line joining the longitudinal axes $2a$ and $3a$ of the first 2 and the second 3 guide members.

This median plane X, when in use, passes through the longitudinal line of the vertebral column of the patient to whom the first 100 and the second 200 vertebra belong.

The first 2 and the second 3 guide members can be overlapped, by juxtaposition, to the first vertebra 100, and united with it by contact only, without a fixed and immovable bond.

Advantageously, the navigation guide 1, which is the subject of the present invention, comprises, in addition to the first 2 and the second 3 guide member, only one additional guide member, specifically a third guide member 6 adapted to being united with the second vertebra 200, which is adjacent and consecutive to the first 100.

Overall, therefore, the guide has only three guide members: a first 2 and a second 3 guide member, which are overlapped, by juxtaposition, and united with the first vertebra 100, and a third guide member 6, which is overlapped, by juxtaposition, and united with the second adjacent vertebra 200. The guide members are not bound integrally with the vertebrae but are only coupled by contact.

The third guide member 6 is integral with the supporting frame 4 thanks to a plate 8 that is only connected to one of the other two guides: to the first 2 or to the second 3 guide member. This plate 8 extends from the supporting frame 4 in the caudal direction, if one considers the guide in the use configuration, from the first vertebra (S01) 100 on which the first 2 and the second 3 guide members rest, to the second vertebra (S02) 200, on which the third guide member 6 rests.

The third guide member 6 also extends along a respective longitudinal development axis $6a$ from a proximal opening $6p$ to a distal opening $6d$.

The third guide member 6 has an internal channel 7, developing along the longitudinal axis $6a$, in which surgical instruments are inserted, such as a Kirschner wire, a cannulated drill bit or a screw, or the like, adapted to operating on the second vertebra of a patient 200.

As can be seen from the attached figures, the longitudinal development axis $6a$ of the third guide member 6 is arranged transversely with respect to the median plane X and to the longitudinal development axes $2a$, $3a$ of the first 2 and the second 3 guide member.

The first 2 and second 3 guide members have longitudinal axes $2a$ and $3a$ converging in the distal direction towards the median plane X, where the distal direction means the one furthest from the patient's spine. In other words, the longitudinal axes $2a$ and $3a$ of the first 2 and the second 3 guide members intersect above the specific navigation guide 1, when considered in use configuration.

In addition, the longitudinal axes $2a$ and $3a$ of the first 2 and second 3 guide members are tilted in the caudal direction, i.e. towards the plate 8, and tend to intersect above the navigation guide when considered in use configuration.

The longitudinal axis $2a$ of the first guide member 2 and the longitudinal axis $3a$ of the second guide member 3 are both skewed with respect to the longitudinal axis $6a$ of the third guide member 6.

The navigation guide 1 also comprises contact surfaces 14, 15, 16 designed to match a corresponding plurality of contact areas 101, 102, 103 that can be identified on the first 100 and second 200 vertebrae of the patient, in order to define a single coupling configuration of the patient-specific navigation guide 1 on the respective vertebrae 100 and 200. In other words, these contact surfaces 14, 15 and 16 are patient-specific and, therefore, follow the anatomical trend of the patient's vertebra, with which they are coupled.

The combination of the tilt of the first 2, second 3 and third 6 guide members and the single coupling of the guide 1 with the vertebrae 100, 200 through the above-mentioned contact surfaces 14, 15 and 16, precisely and unambiguously directs the surgical instrument, which is inserted inside the channel 5 of the first 2 or second 3 guide member or inside the channel 7 of the third guide member 6, to identify a precise and predetermined operating point.

In particular, the contact surfaces 14, 15 and 16 are respectively made beneath the first 2 and second 3 guide members and beneath the plate 8 connecting the third guide member 6 and either the first 2 or the second 3 guide member. The contact surface 16, located beneath the plate 8, also extends beneath the third guide member 6.

The contact areas 101, 102 and 103 of the vertebrae correspond respectively to the surface located laterally to the sacral crest or spinous process of the first vertebra 100 and to one of the two laminae of the second vertebra 200, located at the sides of the sacral crest or spinous process.

In particular, the plate 8 defines a contact surface 103 with the lamina of the patient's vertebra at a proximal surface thereof, i.e. the surface in contact with the patient's vertebra.

The supporting frame 4 comprises a bridge 9 connecting the first 2 and the second 3 guide member. Said bridge 9 preferably has a substantially inverted V shape.

Advantageously, the bridge 9 comprises a main contact member 10 adapted to being coupled to the spinous process or sacral crest of the first vertebra 100.

For better handling, the bridge 9 comprises, substantially above the main contact organ 10 that can be coupled to the spinous process or sacral crest, a gripping element 17, which also serves as a pressure point for keeping the guide in a stable position during the insertion of surgical instruments into the channels of the guide members.

The longitudinal axes 2a and 3a of the first 2 and second 3 guide members are tilted in the caudal direction, i.e. towards the plate 8, and tend to intersect above the gripping element 17 of the bridge 9 of the navigation guide.

Beneath the main contact member 10 of the bridge 9, there is a notch 11 adapted to accommodate the sacral crest or spinous process. This notch 11 is not positioned at the centre of the bridge 9 but is misaligned with respect to the midpoint of the apex of the bridge 9, being placed near the sacral crest or spinous process. In one embodiment, the sacral crest or spinous process is accommodated inside the notch 11 without there being any contact between them. In another embodiment, the sacral crest or spinous process is accommodated inside the notch 11, coming into contact with it. Again, in another embodiment, it is possible to make the notch 11 in such a way that it is specific for the patient, presenting an internal surface shaped so as to perfectly match the morphology of the sacral crest or spinous process of the patient.

Advantageously, in a second aspect, the present invention relates to a patient-specific navigation guide kit comprising two guides 1 as described above.

Figure 2:
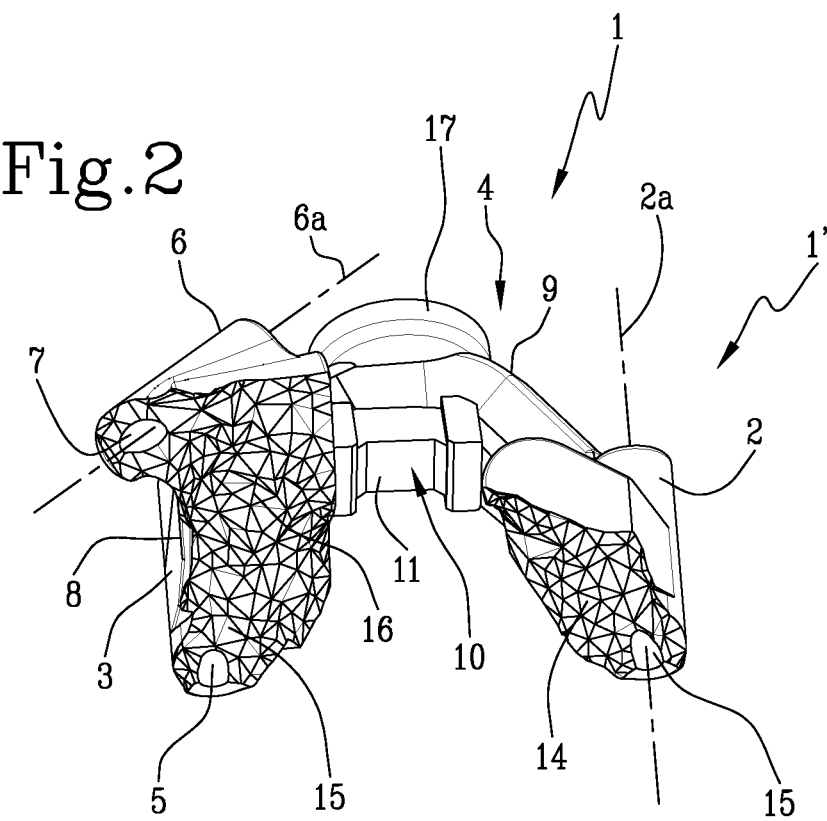
FIG. 2 is a view from below of the guide shown in FIG. 1.
Figure 5:
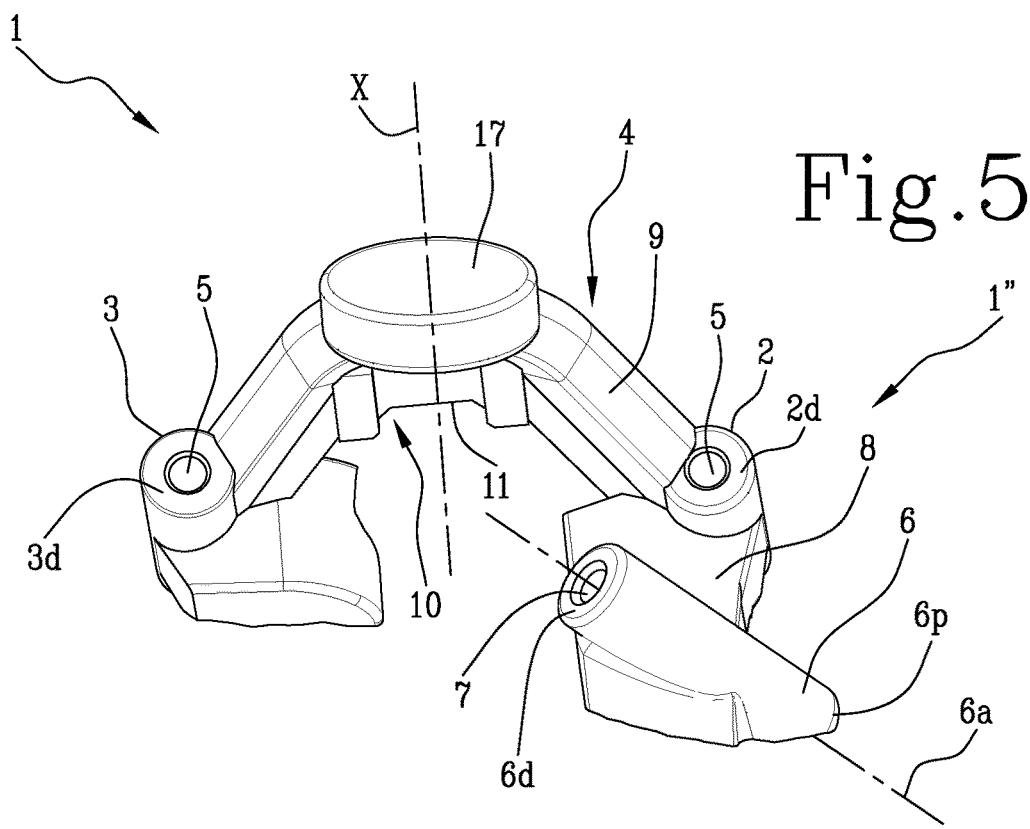
FIG. 5 is a perspective view of a second patient-specific navigation guide according to the present invention.
Figure 6:
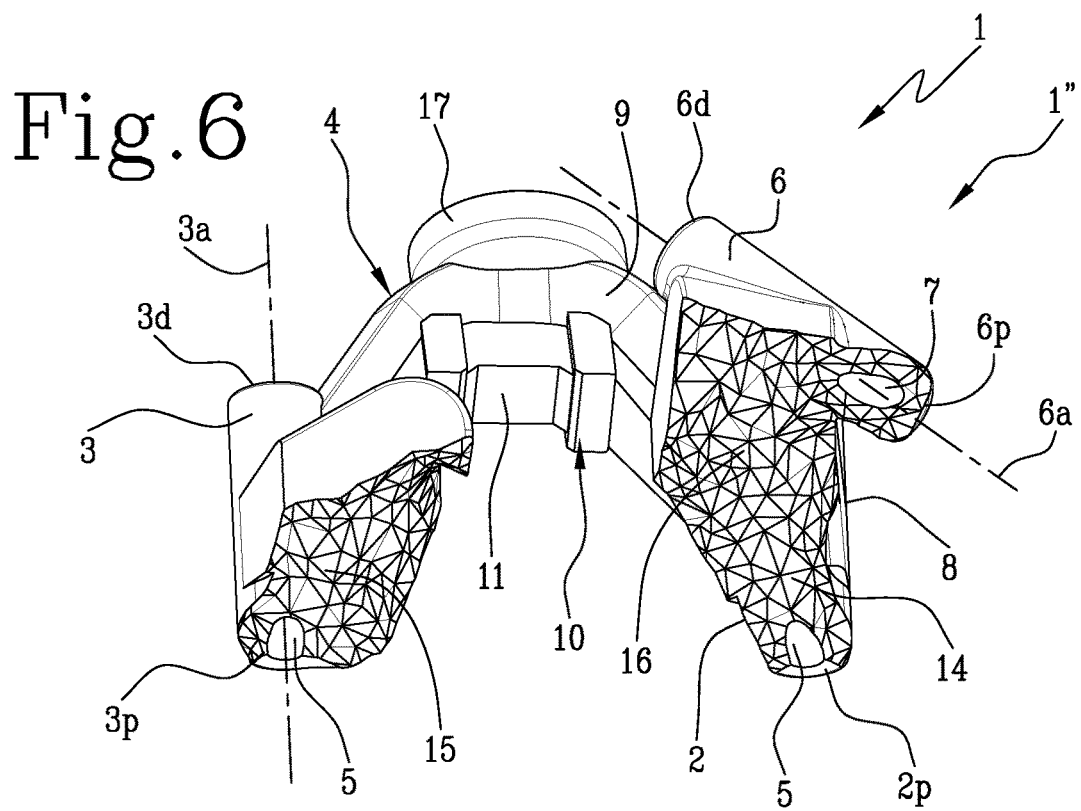
FIG. 6 is a view from below of the guide shown in FIG. 1.
Figure 9:
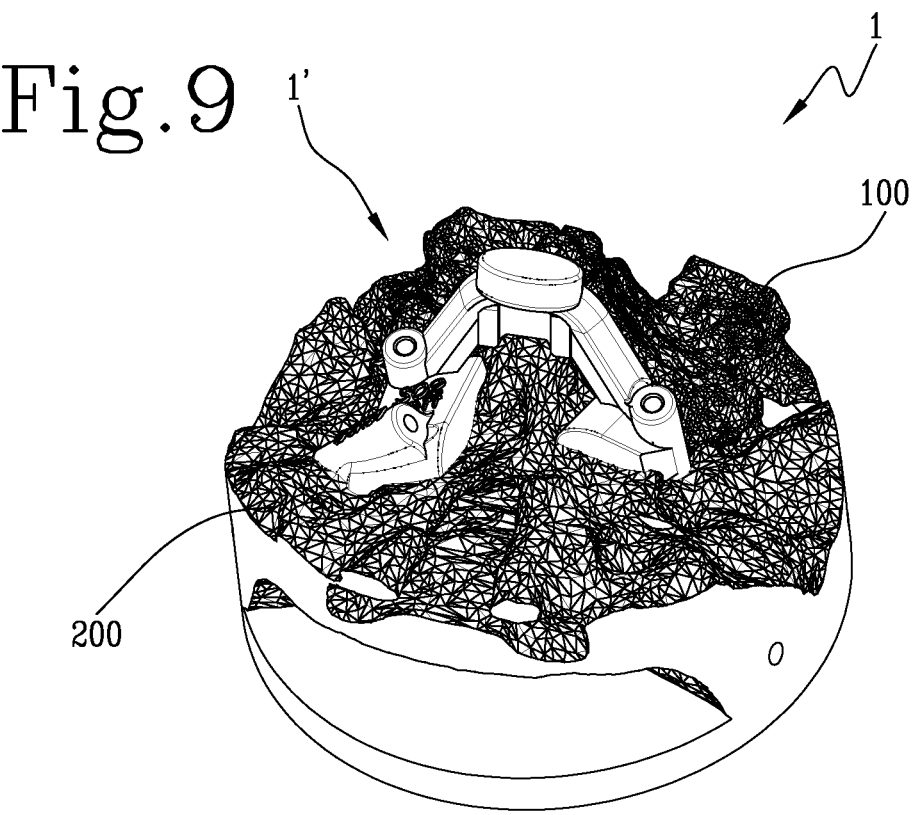
FIG. 9 is a perspective view of the guide in FIG. 1 in use configuration and mounted on the vertebrae of a patient.
Figure 10:
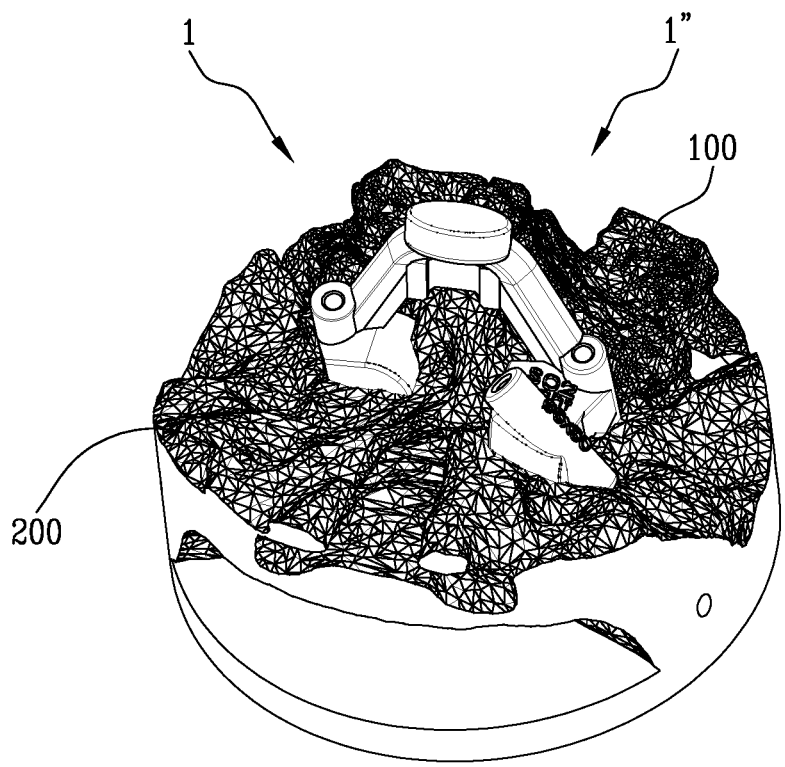
FIG. 10 is a perspective view of the guide in FIG. 5 in use configuration and mounted on the vertebrae of a patient.
Figure 11:
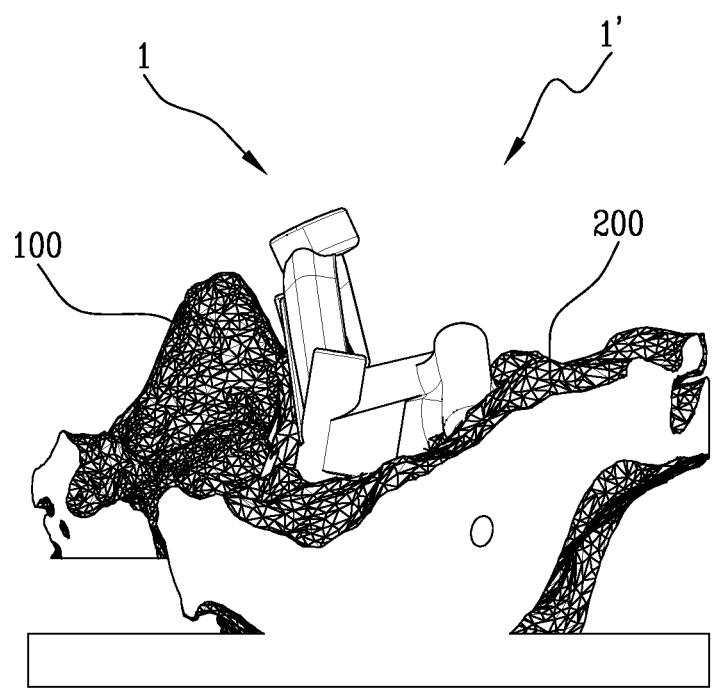
FIG. 11 is a lateral view of the guide shown in use configuration in FIG. 9.

These guides 1 (indicated with 1' and 1" in FIGS. 1-8) are substantially symmetrical to each other: in other words, both have the same structure comprising a supporting frame 4 to which the first 2 and the second 3 guide members are connected. The supporting frame 4 has a bridge 9 equipped with a notch 11, as described above.

Both the guides 1', 1" also comprise only one additional third guide member 6, in addition to the first 2' and the second 3 guide member: the first guide 1' has this third guide member 6 connected through a plate 8 to the first guide member 2 only, while the second guide 1" has this guide member 6 connected through a plate 8 to the second guide member 3 only. Both plates 8 extend in the caudal direction, if you consider the specific navigation guide in use configuration.

In this way, using first the first guide and then the second guide, after having appropriately removed the first guide, it is possible to drill two sides of the second vertebra 200, substantially symmetrical with respect to the longitudinal line of the vertebral column to which the two vertebrae 100 and 200 belong.

In use, the surgeon makes an incision substantially at the L05 vertebra up to the S01 vertebra.

With this device it is possible to not extend the incision up to the S02 vertebra, even though the latter is involved in the surgical process.

By slightly enlarging the wound with the fingers, it is possible to insert the first guide first and to operate on the first vertebra (S01) 100 and on the second vertebra (S02) 200 by inserting the appropriate surgical instruments in their respective channels 5 and 7.

The first 2 and the second 3 guide members act on the first vertebra 100 and can therefore be coupled together by juxtaposition to the latter.

The third guide member 6, on the other hand, acts on the second vertebra 200, adjacent to the first, and is then coupled to it, by juxtaposition.

In other words, the guide members 2, 3 and 6 are not bound integrally with the vertebrae but only coupled to them by contact.

Subsequently, the first guide 1 can be removed and the second guide inserted using the holes already made on the first vertebra (S01) 100, considering that the first 2 and the second 3 guide members of the two navigation guides coincide, and thus inserting the instruments already positioned inside the channels 5 of the first 2 and the second 3 guide members. The surgeon can, thus, operate on the second vertebra (S02) 200 on the opposite side with respect to the median plane X, operating through the third guide member 6 of the second guide.

The invention thus produced allows the predetermined purposes to be achieved.

With the navigation guide described above, it is possible to perform surgical operations on the sacral vertebrae in minimally invasive surgery, since the device has reduced dimensions.

The single guide, in fact, incorporates the holes for surgical instruments adapted to operate on the S01 plus a third hole for the insertion of surgical instruments to the right or left of the S02 vertebra.

The three guide members allow the insertion of surgical instruments with a minimally invasive technique and the larger support surface on the insertion side of the instrument in the S02, to the right for one guide, to the left for the other, ensures greater stability during use.

For this reason, the guide that is the subject of the present invention allows the surgeon to safely and precisely insert the surgical instruments even with difficult trajectories, and without continuous beam control.

Finally, the guide described enables simplified positioning on the patient's bone structure in a stable and safe manner.

The invention claimed is:

1. A patient-specific navigation guide kit for use in spinal surgery comprising:
   a first patient-specific navigation guide and a second patient-specific navigation guide, each navigation guide comprising:
   a first and a second guide member, both integral with a supporting frame and extending along a respective longitudinal development axis from a proximal opening to a distal opening for guiding surgical instruments on a first vertebra of a patient; and
   contact members designed to match with a corresponding plurality of contact areas on a first and on a second vertebra of the patient in order to define a single coupling configuration of the patient-specific navigation guide on the patient's vertebrae,
   wherein said first and second guide members are substantially opposite with respect to a median plane orthogonal to a straight line joining said longitudinal axes of said first and second guide members,
   wherein said guide comprises a third guide member adapted to abut on a second vertebra which is adjacent and consecutive to the first, in such a way that there are only three guide members in total,
   wherein said third guide member of the first patient-specific navigation guide is integral with said respective supporting frame through a plate connected to said respective first guide member, and said third guide member of the second patient-specific navigation guide is integral with said respective supporting frame through a plate connected to said respective second guide member,
   wherein the third guide member of the first patient-specific navigation guide and the third guide member of the second patient-specific navigation guide are symmetrical with respect to the median plane dividing the respective first and second guide members, each third guide member presenting a respective axis inclined towards the median plane and incident above the respective navigation guide.

2. The guide kit according to claim 1, wherein said plate extends from said supporting frame in a caudal direction, considering the guide in use configuration.

3. The guide kit according to claim 1, wherein said guide members are tubular.

4. The guide kit according to claim 1, wherein said third guide member extends along a respective longitudinal development axis from a proximal opening to a distal opening for guiding surgical instruments on said second adjacent vertebra; said longitudinal development axis being transverse to said median plane and being skewed with respect to said longitudinal development axes of said first and second guide members.

5. The guide kit according to claim 1, wherein said plate defines, at a proximal surface thereof, a contact surface configured to contact with the lamina of the second vertebra of the patient in use.

6. The guide kit according to claim 1, wherein said supporting frame comprises a bridge connecting said first and second guide members; said bridge comprising a main contact member adapted to be coupled to the spinous process or sacral crest of the first vertebra.

7. The guide kit according to claim 6, wherein said bridge comprises a gripping element substantially above said main contact member.

8. The guide kit according to claim 6, wherein a notch adapted to accommodate the sacral crest is present beneath the main contact member of the bridge.

* * * * *